US009028840B2

(12) United States Patent
Adhikary et al.

(10) Patent No.: US 9,028,840 B2
(45) Date of Patent: May 12, 2015

(54) EX VIVO METHOD FOR PRODUCING A PREPARATION CONTAINING CD4+ T CELLS SPECIFIC FOR EBV STRUCTURAL ANTIGENS

(75) Inventors: Dinesh Adhikary, Neuried (DE); Uta Behrends, Munich (DE); Josef Mautner, Munich (DE); Henri-Jacques Delecluse, Heidelberg (DE); Regina Feederle, Heidelberg (DE)

(73) Assignees: Helmholtz Zentrum Munchen Deutsches Forschungzentrum fur Gesundheit und Umwelt (GmbH), Neuherberg (DE); Deutsches Krebsforschungzentrum (DKFZ), Heidelberg (DE)

( * ) Notice: Subject to any disclaimer, the term of this patent is extended or adjusted under 35 U.S.C. 154(b) by 990 days.

(21) Appl. No.: 12/744,474

(22) PCT Filed: Nov. 27, 2008

(86) PCT No.: PCT/EP2008/066347
§ 371 (c)(1),
(2), (4) Date: Nov. 29, 2010

(87) PCT Pub. No.: WO2009/068615
PCT Pub. Date: Jun. 4, 2009

(65) Prior Publication Data
US 2011/0059133 A1    Mar. 10, 2011

(30) Foreign Application Priority Data
Nov. 27, 2007 (EP) ..................................... 07121683

(51) Int. Cl.
*A61K 39/245* (2006.01)
*C12N 5/0783* (2010.01)
*A61K 39/00* (2006.01)

(52) U.S. Cl.
CPC ....... *A61K 39/245* (2013.01); *A61K 2039/5158* (2013.01); *A61K 2039/5258* (2013.01); *C12N 5/0636* (2013.01); *C12N 2502/11* (2013.01); *C12N 2710/16234* (2013.01)

(58) Field of Classification Search
CPC ................... A61K 39/245; A61K 2039/5158; C12N 5/0636; C12N 2710/16234; C12N 2502/11
See application file for complete search history.

(56) References Cited

U.S. PATENT DOCUMENTS

| | | | |
|---|---|---|---|
| 5,962,318 A | 10/1999 | Rooney et al. | |
| 6,194,205 B1 * | 2/2001 | Staege et al. | .................. 435/373 |
| 6,291,246 B1 | 9/2001 | Delecluse et al. | |
| 6,436,693 B1 | 8/2002 | Delecluse et al. | |
| 2006/0194203 A1 | 8/2006 | Takada et al. | |

OTHER PUBLICATIONS

Adhikary et al. (Journal of Experimental Medicine, Apr. 2006, vol. 203, p. 995-1006 in IDS on May 24, 2010).*
Adhikary et al. (PloS, Jul. 2007, p. 1-10 in IDS on May 24, 2010).*
Adhikary, D., et al., "Control of Epstein-Barr virus infection in vitro by T helper cells specific for virion glycoproteins," *The Journal of Experimental Medicine*, vol. 203(4), pp. 995-1006 (Apr. 17, 2006).
Adhikary, D., et al., "Immunodominance of Lytic Cycle Antigens in Epstein-Barr Virus-Specific CD4+ T Cell Preparations for Therapy," *PLoS One*, vol. 2(7), e583, 10 pgs. (Jul. 2007).
Adhikary, D., et al., "Standardized and Highly Efficient Expansion of Epstein-Barr Virus-Specific CD4+ T Cells by Using Virus-Like Particles," *Journal of Virology*, vol. 82(8), pp. 3903-3911 (Apr. 2008).
Delecluse, H.-J., et al., "A first-generation packaging cell line for Epstein-Barr virus-derived vectors," *Proc. Natl. Acad. Sci. USA*, vol. 96, pp. 5188-5193 (Apr. 1999).
Delecluse, H.-J., et al., "Epstein-Barr virus-associated tumors: an update for the attention for the working pathologist," *Journal of Clinical Pathology*, vol. 60(12), pp. 1358-1364 (Dec. 2007).
Delecluse, H.-J., et al., "Contribution of viral recombinants to the study of the immune response against the Epstein-Barr virus," *Seminars in Cancer Biology*, vol. 18(6), pp. 409-415 (Dec. 2008).
Feederle, R., et al., "Defective Infectious Particles and Rare Packaged Genomes Produced by Cells Carrying Terminal-Repeat-Negative Epstein-Barr Virus," *Journal of Virology*, vol. 79(12), pp. 7641-7647 (Jun. 2005).
Feederle, R., et al., "Epstein-Barr Virus BNRF1 Protein Allows Efficient Transfer from the Endosomal Compartment to the Nucleus of Primary B Lymphocytes," *Journal of Virology*, vol. 80(19), pp. 9435-9443 (Oct. 2006).
Granato, M., et al., "Deletion of Epstein-Barr Virus BFLF2 Leads to Impaired Viral DNA Packaging and Primary Egress as Well as to the Production of Defective Viral Particles," *Journal of Virology*, vol. 82(8), pp. 4042-4051 (Apr. 2008).
Keever-Taylor, C., et al., "Suppression of EBV release from irradiated B lymphoblastoid cell-lines: superior activity of ganciclovir compared with acyclovir," *Cytotherapy*, vol. 5(4), pp. 323-335 (2003).

(Continued)

*Primary Examiner* — Agnieszka Boesen
(74) *Attorney, Agent, or Firm* — Kilpatrick Townsend & Stockton LLP (57) ABSTRACT

The present invention discloses an ex vivo method for producing a preparation containing CD4+ T cells specific for EBV structural antigens for use in the prophylaxis and treatment of patients with a reduced T cell activity in order to prevent or treat growth of EBV infected B cells.

8 Claims, 7 Drawing Sheets

(56) References Cited

OTHER PUBLICATIONS

Kilger, E., et al., "Virus-free B cell lines expressing mucin (MUC1) gene by transfection with a mini-EBV plasmid," *European Journal of Cancer*, vol. 33, p. S55, Abstract 126 (Jun. 1, 1997).

Lee, S., et al., "MHC class II-restricted presentation of endogenously synthesized antigen: Epstein-Barr virus transformed B cell lines can present the viral glycoprotein gp340 by two distinct pathways," *International Immunology*, vol. 5(5), pp. 451-460 (May 1993).

Lucas, K., et al,. "A Phase I-II Trial to Examine the Toxicity of CMV- and EBV-Specific Cytotoxic T Lymphocytes When Used for Prophylaxis against EBV and CMV Disease in Recipients of CD34-Selected/T Cell-Depleted Stem Cell Transplants," *Human Gene Therapy*, vol. 11(10), pp. 1453-1463 (Jul. 1, 2000).

Milosevic, S., et al., "Identification of Major Histocompatibility Complex Class II-Restricted Antigens and Epitopes of the Epstein-Barr Virus by a Novel Bacterial Expression Cloning Approach," *Journal of Virology*, vol. 80(21), pp. 10357-10364 (Nov. 2006).

Moosmann, A., et al., "Generation of EBV-specific T cells using a non-replicating EBV vector," *Immunobiology*, vol. 210(6-8), p. 430, Abstract H.17 (2005).

Moosmann, A., et al., "B cells immortalized by a mini-Epstein-Barr virus encoding a foreign antigen efficiently reactivate specific cytotoxic T cells," *Blood*, vol. 100(5), pp. 1755-1764 (Sep. 1, 2002).

Moss, P., et al., "Cellular Immunotherapy for Viral Infection After HSC Transplantation," *Nature Reviews. Immunology*, vol. 5(1), pp. 9-20 (Jan. 2005).

Wallace, L.E., et al., "Identification of Two T-Cell Epitopes on the Candidate Epstein-Barr Virus Vaccine Glycoprotein gp340 Recognized by $CD4^+$ T-Cell Clones," *Journal of Virology*, vol. 65(7), pp. 3821-3828 (Jul. 1, 1991).

Zentz, C., et al., "Activated B Cells Mediate Efficient Expansion of Rare Antigen-Specific T Cells," *Human Immunology*, vol. 68(2), pp. 75-85 (Feb. 23, 2007).

Zimmermann, J., et al., "Structure and Role of the Terminal Repeats of Epstein-Barr Virus in Processing and Packaging of Virion DNA," *Journal of Virology*, vol. 69(5), pp. 3147-3155 (May 1, 1995).

Buonaguro, et al., "Virus-like Particles (VLPs) as Anti-viral Vaccines: An Effective Approach for an $HIV_{-1}$, Vaccine Strategy," *ASHI Quarterly*, pp. 78-80 (Jan. 2005).

Chackerian, "Virus-like particles: flexible platforms for vaccine development," *Expert Review of Vaccines*, vol. 6(3), pp. 381-390 (Jun. 2007).

Office Action for European Application No. EP 08855231, 9 pages, dated Mar. 20, 2013.

Delecluse, et al., "Propagation and recovery of intact, infectious Epstein-Barr virus from prokaryotic to human cells," *Proc. Natl. Acad. Sci. USA*, vol. 95, pp. 8245-8250 (1998).

\* cited by examiner

EX VIVO METHOD FOR PRODUCING A PREPARATION CONTAINING CD4+ T CELLS SPECIFIC FOR EBV STRUCTURAL ANTIGENS

CROSS-REFERENCES TO RELATED APPLICATIONS

This application is a U.S. National Stage Application of PCT/EP2008/066347, filed Nov. 27, 2008, which claims priority to European patent application number 07121683.2, filed Nov. 27, 2007, the contents of which are herein incorporated by reference in their entirety.

The present invention refers to an ex vivo method for producing a preparation containing CD4+ T cells which are specific for EBV structural antigens as well as to preparations containing CD4+ T cells specific for EBV structural antigens obtained by said ex vivo method.

BACKGROUND OF INVENTION

The oncogenic Epstein-Barr virus (EBV) belongs to the family of gamma-herpesviruses and establishes lifelong persistent B cell infections in more than ninety percent of the human population (19, 20). In healthy individuals, the majority of EBV-infected B cells show limited viral gene expression and a resting phenotype. Terminal differentiation of latently infected cells into plasma cells leads to virus reactivation, production, and reinfection of B cells (21). Expression of all viral latency genes causes growth transformation and proliferation of infected B cells, which is reflected by the outgrowth of EBV-transformed lymphoblastoid B cell lines (LCL) in vitro and by the association of EBV with a variety of B cell lymphoproliferative diseases including different types of lymphoma in vivo (32). EBV infection is controlled by T cells as indicated by an increased incidence of EBV-associated malignancies in patients with congenital or iatrogenically induced T cell dysfunction (32), and by the successful treatment of EBV-associated post-transplant lymphoproliferative disease (PTLD) in hematopoietic stem cell transplant recipients by the infusion of polyclonal EBV-specific T cell lines (34, 35). Such lines are prepared by repeated stimulation of peripheral blood T cells with autologous LCL and contain CD4+ and CD8+ components. The antigens recognized by the EBV-specific CD8+ T cell component are mostly derived from latent as well as immediate early and early lytic cycle proteins (17). Although CD4+ T cell responses to these antigens have been detected in peripheral blood of EBV-positive donors, CD4+ T cells in LCL-stimulated preparations are almost exclusively directed against late lytic cycle antigens derived from structural proteins of the virus, which are efficiently presented on MHC II following CD21-mediated uptake of EBV particles by B cells (1, 2, 9, 24). Such T cells are cytolytic and able to prevent the proliferation of EBV-infected B cells and to inhibit the outgrowth of LCL from freshly infected B cells (2, 16). Targeting mostly non-overlapping sets of viral proteins and different phases of the virus' life cycle implies that CD4+ and CD8+ T cells complement each other in establishing protective immunity against EBV.

The successful treatment of immanent and manifest PTLD in hematopoietic stern cell transplant (HSCT) recipients by the infusion of EBV-specific T cell preparations has provided an important proof of principle for this form of immunotherapy, but owing to the considerable technical requirements and financial implications of extensive in vitro T cell culture, adoptive T cell therapy still has a limited role in the management of virus-associated complications in HSCT patients (28). Moreover, other EBV-associated malignancies, e.g. nasopharyngeal carcinoma and Hodgkin's disease respond less efficaciously to this form of immunotherapy, most likely because of immune evasion strategies by tumor cells such as non-expression of the EBNA3 family of proteins, the immunodominant targets of the latent antigen-specific CD8+ T cell response (12). To increase clinical efficacy of the T cell preparations and to implement this treatment modality as a conventional therapeutic option, generic and more direct approaches for the generation of EBV-specific T cell lines enriched in disease-relevant specificities need to be developed.

Two recent reports imply an important role of CD4+ T cells in establishing antiviral immunity. First, low endogenous CD4+ T cell numbers have been identified as important risk factors for the development of EBV-associated diseases in immunosuppressed patients (36). Second, patients with PTLD showed better clinical responses in a recent phase II trial when the infused T cell lines contained higher proportions of CD4+ T cells (15). For reasons unknown, the CD4/CD8 ratio in LCL-stimulated T cell preparations may vary from 2:98 to 98:3 (37).

U.S. Pat. No. 6,194,205 describes a method for the stimulation of T cells having a desired antigen specificity. Genes required for immortalization are introduced into antigen-presenting cells (APCs); said immortalising genes are preferably taken from EBV. Column 8 lines 31-32 states the introduction of all EBV immortalizing genes into the cells by P3HR1 virus. The immortalising genes of EBV are present for instance on mini-EBV vectors as described in column 4, lines 39 and 40. Said APCs may be e.g. B cells as described in column 4, line 19. In column 9, line 63 to column 10, line 56 the use of EBV-immortalised LCLs for T cell activation is described. The method described in this US patent is different from the presently claimed method as no virus-like particles of EBV are used. EB virus-like particles do not include any transforming DNA but only EBV structural antigens necessary for virion production. Therefore, the method described in U.S. Pat. No. 6,194,205 suffers from the same drawbacks as all other prior art methods directed to providing CD4+ T cells specific for EBV-structural antigens. No LCLs have to be generated in the present method. Summarizing, U.S. Pat. No. 6,194,205 reports the use of lymphoblastoid cell lines, or continuously growing B cells latently infected by a genetically modified virus as antigen-presenting cells. The viruses present in these cells retain replicative and transforming abilities. This experimental system therefore does not make use of viruses or of virus-like particles that are non-transforming. The present application presents a method that circumvents the use of LCLs the latter being less efficient and less safe than virus-like particles used in the present invention for the generation of EBV-specific CD4-positive T cells.

Moosmann et al: "Generation of EBV-specific T cells using a nonreplicating EBV vector" Immunobiology, vol. 210, no. 6-8, 2005, page 430, describe mini-EBV transformed B cell lines obtained by infection of B cells with EBV-like particles carrying the mini-EBV genome. Second sentence second paragraph states: "However, it encodes the full set of latent genes and can therefore mediate B cell transformation in vitro." This document does also not overcome the prior art disadvantages by using mini-EBV genomes which are not devoid of any transforming viral DNA causing again danger of introducing transforming DNA into the patient. This document does not describe the use of EBV-like particles being devoid of any transforming viral DNA and containing only EBV-structural antigens.

Moosmann et al: "B cells immortalized by a mini-Epstein-Barr virus encoding a foreign antigen efficiently reactivate specific cytotoxic T cells." Blood 1 Sep. 2002, vol. 100, no. 5, 1 Sep. 2002 (2002-09-01), pages 1755-1764, XP002469377 ISSN: 0006-4971 describe mini-EBV-immortalized B cell lines produced by infection of B cells with virus-like particles carrying mini-EBV DNA. The first paragraph of the abstract states: "Previously we constructed a mini-EBV plasmid that consists of less than half the EBV genome, is unable to cause virus production, but still immortalizes in vitro". Only the method described by the present inventors use EB virus-like particles which are devoid of transforming EBV-DNA.

The preparations described in both documents of Moosmann et al. are profoundly different in nature from the virus-like particles and have opposite properties regarding the ability to transform normal B cells: They do not efficiently generate multiple CD4-positive EBV-specific T cell clones. As a matter of fact, these preparations are unable to stimulate immune responses against EBV structural antigens due to the genetic alterations that were introduced into the mini-EBV genome. They further contain large amounts of transforming viral DNA. The documents of Moosmann et al. and US '205 disclose so-called "virus-like particles" which are fully infectious EB viruses containing mini-EBV, a genetically modified genome that fully retains its transforming capabilities. Contrary thereto, the invention describes the use of mature intact EB virions devoid of transforming viral DNA.

Feederle R. et al: "Epstein-Barr virus BNRF 1 protein allows efficient transfer from the endosomal compartment to the nucleus of primary B lymphocytes." Journal of Virology, October 2006, vol. 80, no. 19, October 2006 (2006-10), pages 9435-9443, XP002469378 ISSN: 0022-538 X describe the use of mini-LCLs which are primary B cells transformed by mini-EBV. The EBV-like particles disclosed therein are not devoid of any DNA but still contain the mini-EBV genome. One of the major drawbacks of the prior art, namely to avoid the introduction of transforming EBV-DNA into the patient, is not solved by Feederle et al. Only the present inventors have found that EB virus-like particles containing only structural proteins and no transforming DNA can be efficiently used to generate a preparation containing B cells presenting EBV-structural antigens in a method to prepare CD4+ T cells specific for EBV-structural antigens. The results referred to were obtained with a virus that lacks the BNRF1 gene. This BNRF1-null virus contains normal amounts of viral DNA. Additionally, the EB-VLPs of the invention lack the terminal repeats but preferably not BNRF1. The ability to produce virus-like particles (i.e. virions devoid of transforming viral DNA) is restricted to the viral mutant devoid of terminal repeats, an additional element not present in the BNRF1-null mutant described in Feederle et al.

Summarily, none of the above-discussed documents, neither taken alone nor in combination with each other, render the method of the present invention obvious. None of the methods described in the prior art documents disclose the use of Epstein-Barr virus-like particles which are devoid of transforming viral DNA and which contain EBV-structural antigens in a method to obtain a population of CD4+ T cells which is specific for the structural antigens of the Epstein-Barr virus and avoiding the problem of introducing transforming genes into the patient.

It is a problem of the present invention to provide a method for a simple, efficient and rapid preparation of T cell lines specific for EBV in order to receive a population of CD4+ T cells specific for structural antigens of EBV and free of any potentially contaminating EBV capable of infecting and transforming human B cells.

SUMMARY OF THE INVENTION

The invention is based on the discovery that Epstein-Barr virus-like particles (EB-VLPs) containing EBV structural antigens can be used to obtain CD4+ T cells specific for EBV structural antigens. By loading B cells with EB-VLPs, the complete repertoire of structural antigens is presented on MHC II. B cells loaded with EBV are, therefore, the ideal stimulating cells for isolating EBV specific CD4+ T cells ex vivo and for an efficient expansion of these cells in vitro. Due to the high risk of a potential transfer of transforming EBV viruses to a patient, the use of wild type EBV is prohibited. Virus-like particles (VLPs) are intact Epstein-Barr virions devoid of transforming viral DNA and therefore unable to immortalise B cells as shown by Feederle et al., J. Virol. 79:7641-7, 2005 (9). Hence, VLPs do not pose a health risk to patients. As wildtype EBV particles, EB-VLPs contain all structural proteins of EBV and these are efficiently presented on MHC II following receptor-mediated uptake by B cells.

In accordance with the invention a preparation containing CD4+ T cells specific for EBV structural antigens is prepared in an ex vivo method. B cells are incubated with preparations of Epstein-Barr virus-like particles containing EBV structural antigens for a time period sufficient to generate a preparation containing B cells displaying EBV structural antigens on MHC II. Said B cells presenting EBV structural antigens are mixed with a preparation containing T cells and particularly including CD4+ T cells. Said admixture is incubated for a period of time sufficient to obtain a preparation including CD4+ T cells which are specific for EBV structural antigens. Said CD4+ T cells specific for EBV structural antigens are expanded and isolated to obtain a population of CD4+ T cells specific for EBV structural antigens.

Other features and advantages of the invention will be apparent from the following detailed description, claims and figures.

BRIEF DESCRIPTION OF THE DRAWINGS

FIG. 1

Virus Production by LCLs Varies Inter- and Intra-Individually.

(A) The number of viral particles in the supernatants of LCLs from five healthy donors (TG, MS, SM, CH, and IE), and from a patient with acute EBV-associated infectious mononucleosis (IM3), and supernatant of the EBV-producer cell line B95.8 was determined by quantitative PCR using BALF5-specific primers. Viral titers are given as EBV genome equivalents (geq)/ml. (B) The same EBV-positive target cells were tested for recognition by the BLLF1-specific CD4+ T cell clone 1D6. Because none of the target cells expresses the restricting MHC class II molecule, the T cells recognized the target cells only after co-culture with mini-LCL JM which express the restricting MHC allele but are incapable of producing viral particles. T cell recognition of the cell mixtures was target cell-dependent but correlated with the amount of geq detected in the culture supernatant as quantified by PCR. (C) Mini-LCL JM were co-cultured for 24 h with the MHC-mismatched LCL GB that had been cultured for different periods of time in vitro (T1 and T2). Subsequently, the cell mixtures were probed for recognition by the BLLF1-specific CD4+ T cells from donor JM (clone 1D6). As control, T cell recognition of autologous LCL JM, autologous mini-LCL JM and allogeneic LCL GB is shown.

FIG. 2

The Presentation of Structural Antigens of EBV is Impaired After Acyclovir Treatment of LCL.

Autologous LCL and mini-LCL DA, and the MHC-mismatched LCL JM and LCL TG, that had been left untreated or treated with 200 µM acyclovir (ACV) for two weeks, were tested for recognition by CD4+ T cells specific for the virion antigen BNRF1. In addition, the allogeneic lines were co-cultured for 24 h with autologous mini-LCL DA and then tested for T cell recognition. Except for LCL DA, none of the LCL was recognized by the T cells directly. However, the cell mix of autologous mini-LCL DA and allogeneic LCL was recognized, but acyclovir treatment of the LCL abolished recognition. For specificity control, the T cells were also tested for recognition of autologous mini-LCL pulsed with the relevant (BNRF1) or an irrelevant EBV protein (EBNA3C).

FIG. 3

In LCL-Stimulated CD4+ T Cell Preparations, Responses to FCS Dominate Over Virus-Specific Responses.

CD4+ T cell lines were established from EBV-positive donors by repeated stimulation with autologous LCL cultured in media supplemented with either 10% FCS (LCL-FCS) or 10% human serum (LCL-HS) and tested against both types of stimulator cells in cytokine secretion assays. CD4+ T cell lines that had been stimulated with LCL-FCS failed to recognize LCL-HS, suggesting that the lines recognized predominantly antigens derived from FCS. By contrast, CD4+ T cell lines that had been stimulated with LCL-HS recognized both types of target cells, indicating that this line recognized viral or cellular antigen(s).

FIG. 4

Presentation of Exogenous Viral Structure Antigens is Impaired by Human Serum Components.

(A) LCL grown in media supplemented with either 10% FCS (LCL-FCS) or human serum (LCL-HS) were tested for recognition by BLLF1-specific CD4+ T cells (clone 1D6). T cell recognition was reduced when LCL were cultured in human serum. (B) Mini-LCL grown in FSC-containing media were pulsed with increasing amounts of virus supernatant that had been left untreated or incubated at a final concentration of 10% with human serum from an EBV(+) or EBV(−) donor for two hours. Recognition of the cells by BLLF1-specific CD4+ T cells (clone 1D6) was assayed 24 h later.

FIG. 5

Mini-LCL Pulsed with Either VLP or wtEBV are Recognized by Virion-Antigen-Specific CD4+ T Cells with Similar Efficiency.

(A) Mini-LCL JM were pulsed with supernatants from 293/TR− and 293/2089 cells, containing $1 \times 10^7$/ml VLP or wtEBV particles, respectively, and then tested for recognition by autologous BLLF1-specific CD4+ T cells. Over the whole concentration range analyzed, wtEBV and VLP-pulsed mini-LCL were recognized by the T cells to the same extent. (B) The concentration of VLP and wildtype EBV in the supernatants used in (A) was determined by Western blot analysis using an antibody against the tegument protein BNRF1.

FIG. 6

EBV Structural Antigen-Specific CD4+ T Cells are Efficiently Expanded from Peripheral Blood of Healthy EBV Carriers by Repeated Stimulation with VLP-Pulsed PBMC.

(A) Autologous PBMC pulsed with VLP for 24 h were used for repeated stimulation of peripheral CD4+ T cells of donors DA, JM and GB. After five stimulations, all CD4+ T cell lines recognized VLP-pulsed but not or barely unpulsed PBMC, suggesting that these T cells recognized virion antigens. (B) When tested against autologous LCL and mini-LCL, these CD4+ T cell lines showed much stronger responses against LCL, indicating that the VLP-stimulated T cells recognized antigens that were also presented by LCL. (C) After four to six rounds of VLP-stimulation, CD4+ T cells became increasingly EBV-specific as indicated by increasing reactivity against VLP-pulsed autologous PBMC and autologous LCL and decreasing reactivity against unpulsed autologous PBMC. Results for donor JM are shown as an example. (D) To define the antigens recognized by the VLP-stimulated CD4+ T cell lines, mini-LCL were pulsed separately with three structural proteins of EBV (BALF4, BNRF1, and BLLF1) and a non-structural lytic cycle protein of EBV (BALF2). While none of the lines responded against BALF2, each line responded against at least one structural protein.

FIG. 7

Clonality and Specificity of VLP- and LCL-Stimulated CD4+ T Cell Lines.

(A) Peripheral blood CD4+ T cells from donor GB were stimulated six times with either autologous LCL-HS or VLP-pulsed autologous PBMC and then analysed for T cell receptor V beta expression by PCR and subsequent Southern Blot hybridisation of the PCR products. T cell lines stimulated with VLP-pulsed PBMC were oligoclonal at this passage, while LCL-stimulated T cell lines were still polyclonal. (B) CD4+ T cell clones were generated by limiting dilution from T cell lines of donor GB at passage six after stimulation with either VLP-pulsed PBMC or LCL-HS. The specificity of the clones was determined by assessing their reactivity against autologous LCL and mini-LCL. After stimulation with VLP-pulsed PBMC, the majority of clones were specific for EBV lytic cycle proteins as indicated by their exclusive reactivity against LCL. By contrast, most of the T cell clones obtained from the LCL-stimulated T cell line recognized both types of target cells and thus were not specific for EBV lytic cycle antigens.

DETAILED DESCRIPTION OF THE INVENTION

The invention relates, in part, to the newly discovered use of virus-like particles of Epstein-Barr virus for obtaining a population of CD4+ T cells which are highly specific for structural antigens of EBV.

In accordance with the invention Epstein-Barr virus particles are provided. Virus-like particles of EBV are composed of the structural proteins of an Epstein-Barr virus. While these particles resemble the virus from which they were derived, they lack viral DNA. Hence VLPs have lost their ability to infect and transform their target B cells.

Generally all structural antigens of EBV are included into the EB-VLPs. One method on how to produce Epstein-Barr virus-like particles is disclosed in reference (9). The content thereof is fully incorporated herein by reference. In short, packaging of viral DNA is blocked by deleting the terminal repeats located at the end of the linear EBV DNA. It has been found that these viral particles substantially devoid of viral DNA are nevertheless able to bind to B cells as EBV target cells. Viral DNA packaging is shown to be not a prerequisite for virion formation and egress. Other methods of obtaining EB-VLPs may be used and developed further on. One option would be the use of non-genetic methods, e.g. the isolation of EB-VLPs. which are occasionally produced during the "normal" lytic cycle of EBV wherein the isolation is performed by e.g. density gradient centrifugation. In one embodiment of the invention, EB-VLPs include BNRF-1 gene.

Epstein-Barr virus-like particles devoid of transforming DNA and containing all EBV structural antigens necessary for virion production are then incubated with B cells. The B cells can be obtained in one embodiment of the present invention from established B cell lines which are publicly available, e.g. by ATCC or DSMZ (for example the B cell lines DG75 or Ag876 which are publicly available from various sources). In a preferred embodiment of the invention, primary B cells are used, particularly primary B cells contained in peripheral blood mononuclear cells which contains lymphocytes and monocytes. Methods on how to obtain PBMCs are well known in the art. These cells are often extracted from whole blood using ficoll, a hydrophilic polysaccharide that separates layers of blood, with monocytes and lymphocytes forming a buffy coat under a layer of plasma. This buffy coat contains the PBMCs. In short, the method focuses on isolating lymphocytes and monocytes and separating them from red blood cells and granulocytes.

The B cells containing preparation and the EB-VLPs are incubated together for a period of time which is sufficient to generate a preparation containing B cells presenting EBV structural antigens. The viral particles bind to receptors expressed on B cells. Following internalization, virion proteins are digested in lysosomes and endosomes and peptide antigen fragments of EBV structural proteins are bound to MHC II molecules and presented on the B cell's surface. This way of presentation is extremely efficient. Already one virus particle per B cell is sufficient to be recognized by structural antigen-specific CD4+ T cells. By using this method, all structural antigens of an EBV particle are internalised by the B cells and are presented together with MHC II proteins.

Said preparation containing B cells presenting EBV structural antigens is then contacted with a preparation containing T cells including CD4+ T cells. In a preferred embodiment of the invention, said CD4+ T cells containing preparation is obtained from the autologous, in a further embodiment from an allogeneic donor. In a further preferred embodiment, said primary B cells are obtained from an autologous donor.

In order to obtain a sufficient stimulation of said T cells, they are contacted several times, at least two times, preferably 4-8 times, with said preparation containing B cells, presenting EBV structural antigens. Said method can generally be described as follows: PBMCs or B cells (preferably obtained from PBMCs) are contacted with EB-VLPs for a time sufficient to start the stimulation. One preferred time period is about 24 hours. The time period can be modified in accordance with the patient and the sample to be treated. Subsequently the cells are treated, particularly by irradiation in order to stop their ability to proliferate.

In a next step the B cells containing preparation is co-cultivated with PBMCs containing CD4+ T cells or with CD4+ T cells preferably isolated from said PBMCs for a time period sufficient for the expansion of EBV specific CD4+ T cells. The time period is from 8 to 12 days, e.g. for about 10 days. Other time intervals may be used whenever appropriate. During said incubation time, EBV specific CD4+ T cells proliferate while non-EBV specific T cells die. After said incubation period, the living T cells are harvested. Said incubation with EB-VLPs loaded and irradiated B cells is repeated several times, preferably about 3-5 times, particularly preferred 4 times. The following incubations are again each about 10 days or any other time period appropriate. By using this method, T cell lines are obtained which are essentially directed against EBV antigens and which mainly include CD4+ T cells. Summarily, said admixture of B cells presenting EBV structural antigens is contacted with a preparation containing T cells including CD4+ T cells and is incubated for a sufficient period of time (about 10 days). By contacting said B cells loaded with VLPs, said CD4+ T cells are activated and expanded. An accumulation of EBV structural antigens specific T cells, particularly CD4+ T cells and a depletion of non-EBV specific T cells is achieved compared to the starting admixture. However, it is also possible to perform a targeted enrichment of activated CD4+ T cells. Examples thereof are known in the art. Without being bound to a particular method, cytokine secretion and capture assay or isolation of CD40-L positive cells by FACS are mentioned. CD40-L is a protein that is primarily expressed on activated T cells being a costimulatory molecule inducing activation in antigen present cells like B cells in association with T cell receptors stimulated by MHC II molecules on a B cell.

The cytokine secretion and capture assay is available e.g. from Miltenyi Biotec. In short, said CD4+ T cells described above are incubated with a bispecific antibody directed against CD45 (a surface marker for lymphocytes) and against a cytokine secreted by T cells after activation (e.g. interferon gamma). T cells labelled with said antibody are activated during co-cultivation with B cells loaded with EB-VLPs. About 12-16 hours after antigen recognition, said T cells secrete cytokines. These cytokines bind immediately to said antibodies bound to the cell's surface. Subsequently a second antibody (e.g. coupled to magnetic Fe particles) is added to the cells. Said second antibody is directed against the same cytokine (e.g. IFN gamma), however against a different epitope; thereby both antibodies are able to bind the same cytokine molecule. By using this method, T cells having secreted said cytokine (EBV structural antigen specific T cells) can be separated by e.g. magnetic means from T cells unspecific for EBV antigens. This optional step accelerates enrichment of EBV specific T cells.

In a preferred embodiment of the invention, said T cells are obtained from a B cell donor and are, therefore, autologous. Said T cells are obtained preferably from PBMCs. It is feasible to use either said PBMCs directly or to isolate said CD4+ T cells from said PBMCs.

The method of the invention allows enrichment of CD4+ cells by expansion and isolation of said cells. Expansion and isolation are method steps occurring simultaneously. The step of contacting the EBV structural antigens with said T cells activates said T cells followed by proliferation of said CD4+ T cells. Simultaneously T cells not specific for EBV structural antigens are lost as those T cells are not activated. Hence depletion of non EBV specific T cells and isolation of CD40+ T cells are achieved.

The presently claimed method offers a variety of benefits compared to the prior art methods of establishing CD4+ T cells in LCL-stimulated preparations. Using B cells, particularly primary B cells having been contacted and loaded with EB-VLPs for stimulating the expansion of CD4+ T cells, obviates the need to generate LCLs. Establishing T cell lines containing a large population of CD4+ T cells is thereby shortened by about six weeks.

The prior art methods comprising expanding structural antigen specific CD4+ T cells by LCL directed stimulation greatly varies between individual patients. This is partly due to quantitative differences in virus production by LCL. In order to suppress or avoid transfer of viruses from LCL in patients, antiviral drugs like acyclovir are used to inhibit virus production. Using these antiviral agents lead to a decreased presentation of structural antigens of EBV and to retarded expansion of EBV structural antigen specific T cells.

In accordance with the present invention, B cells, particularly, primary B cells are incubated and loaded with a defined amount of EB-VLPs. These standardised simulation conditions facilitate an efficient expansion of EBV structural antigen specific CD4+ T cells of different donors. The present method reduces the time for establishing CD4+ T cell lines specific for EBV structural antigens by several weeks. By combining the method of the present invention with methods for the enrichment of T cells (CD4+ T cells) stimulated by antigens as described before, EBV specific T cells can be isolated directly from peripheral blood of stem cell donors and can be immediately used for the prophylaxis and treatment of LPD in patients after allogeneic stem cell transplantation.

In accordance with the prior art known LCL stimulation, autoreactive T cells are expanded together with EBV specific T cells (Adhikary et al., 2007). Hence LCL stimulated T cells do contain not only EBV specific components but also autoreactive components. Contrary thereto, the present invention provides a method wherein only EBV specific T cells can be detected after stimulating B cells with EB-VLPs. The T cells obtained by the method of the present invention offer not only a higher therapeutic potential but do also provide a lower risk of inducing an autoimmune response.

The present invention also describes a preparation containing CD4+ T cell specific for EBV structural antigens, which is obtained by anyone of the methods described herein. This preparation is preferably used in the prophylaxis and treatment of patients with a reduced T cell activity in order to prevent or treat growth of EBV infected B cells. The patients may be infected with HIV or may be immunosuppressed after having received a transplant, particularly a solid organ or haematopoietic stem cells.

Protective immunity against EBV probably requires CD4+ and CD8+ T cell components. VLP-pulsed PBMC are unlikely to stimulate virus-specific CD8+ T cells, first because B cells are incapable of cross-presenting exogenous antigens on MHC class I (3), and second because EBV-specific CD8+ T cells barely target virion antigens (31). In order to obtain EBV-specific T cell lines containing CD4+ and CD8+ components, the VLP-stimulation approach may either be combined with conventional LCL-stimulation protocols, for example by using acyclovir-treated LCL pulsed with VLP as stimulators, or with peptide stimulation approaches. The EBV-specific CD8+ T cell response is well characterized and immunodominant epitopes have been defined for different HLA alleles (17, 22, 32). Using PBMC pulsed with these peptides as stimulators would obviate the lengthy procedure of generating LCL and significantly shorten the T cell preparation process, which is critical due to the often rapid progression of PTLD. In addition, LCL-stimulated T cell lines are often dominated by CD8+ T cells specific for epitopes derived from the EBNA3 family of proteins, but most EBV-associated tumors fail to express these proteins. Thus, VLP and peptide-based stimulation protocols may not only shorten the preparation process but also increase clinical efficacy of EBV-specific T cell preparations against PTLD and potentially other EBV-associated malignancies like Hodgkin's disease and nasopharyngeal carcinomas.

This invention is further illustrated by the following examples which should not be construed as limiting. The contents of all references cited throughout this application are incorporated herein by reference.

EXAMPLES

Materials and Methods

Materials of Human Origin

The use of materials of human origin for this study was approved by the ethics committee of the Munich University of Technology. Blood samples were obtained from healthy adult volunteers by venopuncture following informed consent.

Cell Culture

Peripheral blood mononuclear cells (PBMC) were purified by Ficoll-Paque (GE Healthcare) density centrifugation. All LCL and mini-LCL were established by infection of primary B cells with wild-type (wt) EBV produced by the B95.8 cell line or with mini-EBV, a genetically engineered virus mutant, as described (2, 27). The VLP-producer cell line TR− has been established by stable transfection of HEK293 cells with an EBV mutant lacking the terminal repeats (8). As a control HEK293 has been transfected with wtEBV-DNA resulting in the cell line 293/2089. LCL and mini-LCL were grown as suspension cultures in RPMI 1640 supplemented with 10% FCS, 1% nonessential amino acids, 1 mM sodium pyruvate, 2 mM L-glutamine, and 50 µg/ml gentamicin. In some experiments FCS was replaced by individual or pooled human serum as indicated. HEK293 transfectants were cultivated as adherent cultures in RPMI 1640 supplemented with 10% FCS, 1% nonessential amino acids, 1 mM sodium pyruvate, 2 mM L-glutamine, and 100 µg/ml hygromycin. T cells were grown in 24-well plates in T cell media consisting of AIM-V lymphocyte media (Invitrogen) supplemented with 10% pooled human serum, 2 mM L-Glutamine, 10 mM HEPES, and 50 µg/ml gentamicin. Peripheral blood CD4+ T cells were separated from PBMC using β-CD4-MicroBeads and MACS columns (Miltenyi Biotec). The gp350/BLLF1- and BNRF1-specific CD4+ T cell clones 1D6 and 1H7 had been generated by repeated stimulation of peripheral CD4+ T cells with protein-pulsed PBMC as described (2, 23).

T Cell Recognition Assays

If not stated otherwise, T cell recognition assays were performed by co-culturing $1 \times 10^5$ target cells and $1 \times 10^5$ T cells for 20 h in 200 µl T cell media in 96-well flat bottom plates as described (2). Cytokine release by the T cells was measured by ELISA following the protocol of the manufacturer (R&D Systems). In cell mixing experiments, LCL were preincubated with mini-LCL at a 1:1 ratio for 24 h prior to the addition of T cells. In some experiments PBMC or mini-LCL were pulsed for 24 h with recombinant proteins, wtEBV or VLP.

TCR-Analysis

Analyses of the T cell receptor (TCR) Vβ-chain variable region were performed by Vβ-chain specific PCR followed by Southern blot hybridization of the PCR products using a Vβ common region-specific radioactive probe (14).

Purification, Titration and Concentration of Viral Particles

Viral supernatants were obtained from densely grown cultures of the marmoset cell line B95.8 (wtEBV), or the BZLF1-transfected HEK293-derived cell lines 293/2089 (wtEBV) and 293/TR− (VLP) (7, 10). The concentration of wtEBV in B95.8 and 293/2089 in the filtered (0.8 µm) supernatants was determined by quantitative real-time PCR using primers specific for the viral BALF5 gene. To determine the concentration of VLP in TR− supernatants, viral particles were pelleted from 5 ml supernatant by ultracentrifugation (2 h at 30,000×g), denatured in Laemmli buffer, the proteins separated by SDS-PAGE, electroblotted onto a nitro-cellulose membrane (Hybond ECL, GE Healthcare), and hybridized with a rabbit polyclonal antibody specific for the viral tegument protein BNRF1. Titered 293/2089 supernatant was used as standard.

Flow Cytometry

For flow cytometry cells were washed in ice cold FACS buffer (PBS with 1% BSA and 0.05% sodium azide), incubated with fluorescence-labelled antibodies for 20 minutes on ice, washed twice with FACS buffer, resuspended in 500 µl ice cold FACS buffer containing 0.5 mg/ml propidium iodide and analysed in a BD FACScan using the CellQuest software.

Recombinant Protein Expression, Purification and Quantification

Recombinant EBV proteins were expressed as C-terminally histidine tagged proteins in HEK293 cells using calcium phosphate or polyethylenimine transfection methods (29). The extraction, purification and quantification of recombinantly expressed proteins has been described previously (1).

Generation of VLP-Reactive CD4+ T Cell Lines

VLP-stimulation of CD4+ T cells was performed by incubating PBMC with a 10-fold excess of VLP prepared in serum-free media for 24 h. Subsequently the cells were irradiated (40 Gy), washed, and co-cultured with an equal number of CD4+ T cells. After 24 h, 50 U/ml IL-2 were added and expanding cultures split as needed. The lines were restimulated every two weeks in the same fashion.

Results

1. The Rate of Spontaneous Virus Production in LCL Cultures Varies Inter- and Intra-Individually.

Figure 1:
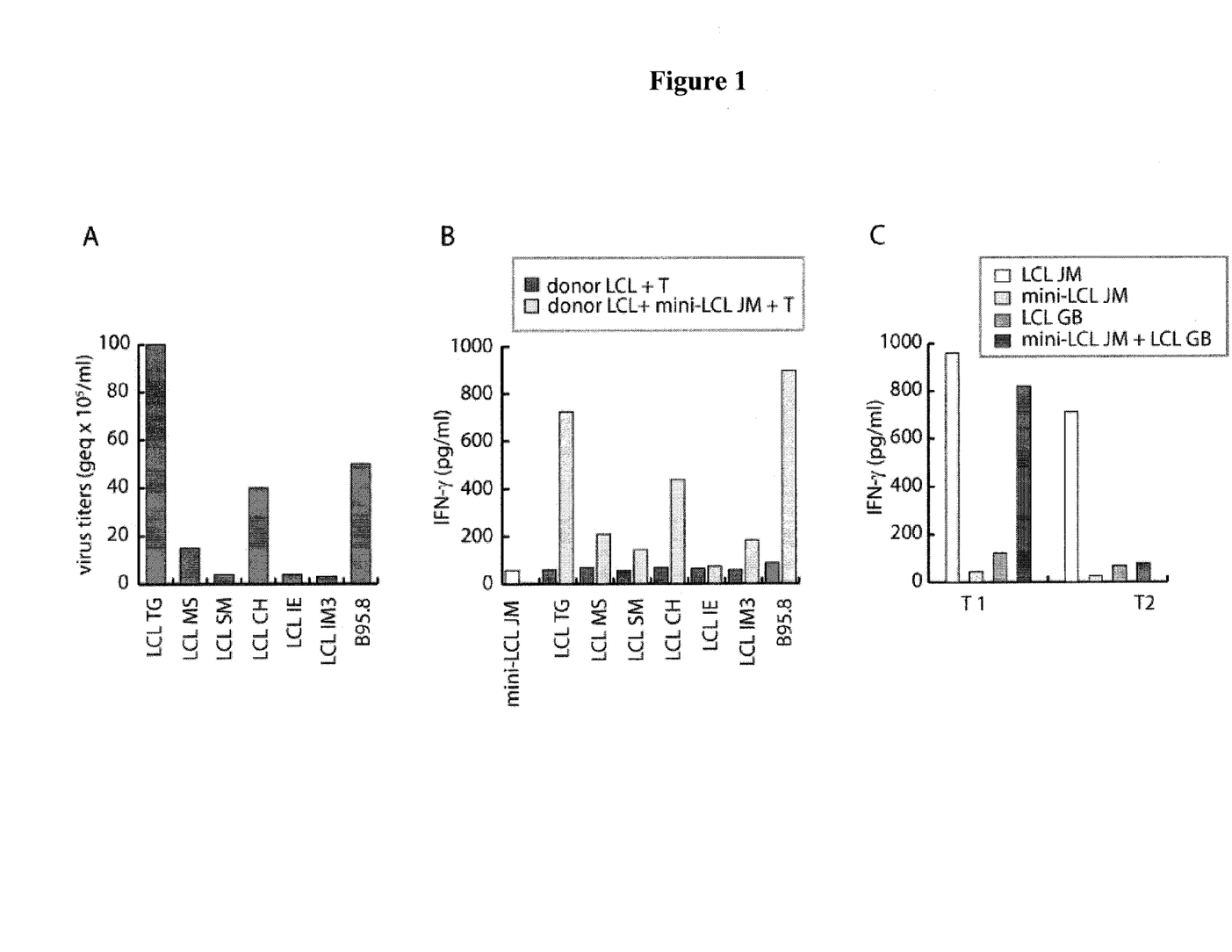

Earlier results of our group had indicated that structural antigens of EBV are the immunodominant targets of LCL-stimulated CD4+ T cells (1). Structural antigens are efficiently presented to CD4+ T cells following CD21-mediated uptake of released virus particles (2). To assess whether differences in the CD4/CD8 composition of LCL-stimulated T cell lines are a reflection of differences in spontaneous virus production among different stimulator LCLs, the concentration of virus particles in the supernatants of several LCLs was measured by two methods. The concentration of packaged virus DNA in supernatants was determined by quantitative PCR using primers specific for the viral gene BALF5 (10, 18) (FIG. 1A), and the amount of transferable antigen in the supernatant was assessed in co-culture experiments using T cells specific for the structural antigen BLLF1 (FIG. 1B). Both assays consistently detected significant fluctuations in virus production. As quantified by PCR, the amount of viral particles in the supernatant of different LCLs varied more than 40-fold. Moreover, spontaneous virus production also varied intra-individually over time. When different passages of the same LCL were tested, striking differences in the amount of transferable antigen were detected in the supernatants (FIG. 1C). These results were paralleled by similar differences in the recognition of these LCLs by lytic cycle antigen-specific CD8+ T cells (data not shown). These results showed that spontaneous virus production in LCL cultures may greatly vary inter- and intra-individually. Since low virus production remained undetected by T cells, such variation may affect the reactivation and expansion of EBV-specific CD4+ T cells by LCL stimulation.

2. Acyclovir-Treatment Impairs the Presentation of Virion Antigens by LCL

Figure 2:
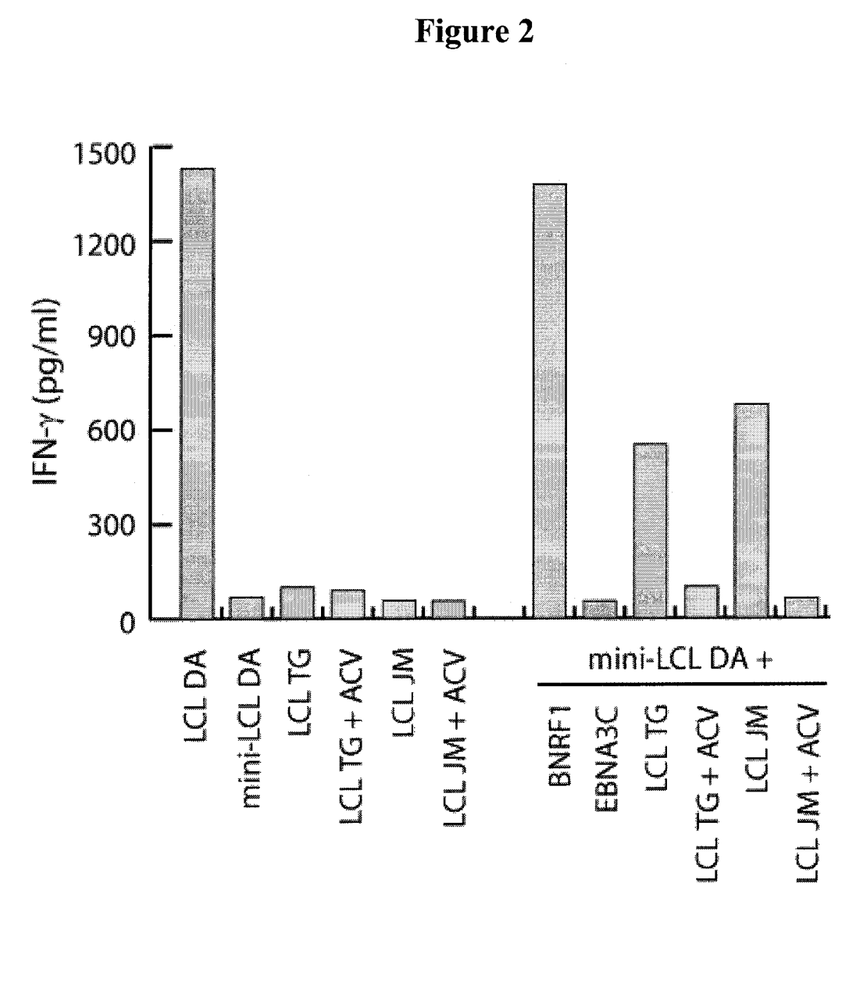

To preclude transfer of infectious virus into patients, T cell lines for clinical use are usually prepared by stimulation with acyclovir-treated LCL. Because acyclovir limits virus production by interfering with late lytic cycle protein expression (6, 19), we assessed virus production in LCL cultures by co-culturing mini-LCL with allogeneic LCL that had been left untreated or treated with acyclovir for two weeks. As compared to untreated LCL, recognition of acyclovir-treated allogeneic LCL by T cells specific for the late lytic cycle antigen BNRF1 was severely impaired demonstrating that treatment of LCL with this drug selectively diminishes the presentation of late lytic cycle antigens (FIG. 2). T cell recognition was reduced to background levels in acyclovir-treated EBV low-producer LCLs, and severely reduced but still detectable in EBV high-producer LCLs (data not shown). Thus, acyclovir treatment may impede the ex vivo expansion of EBV-structure antigen-specific CD4+ T cells and thereby contribute to the fluctuations in the CD4/CD8 composition of LCL-stimulated T cell lines.

Figure 3:
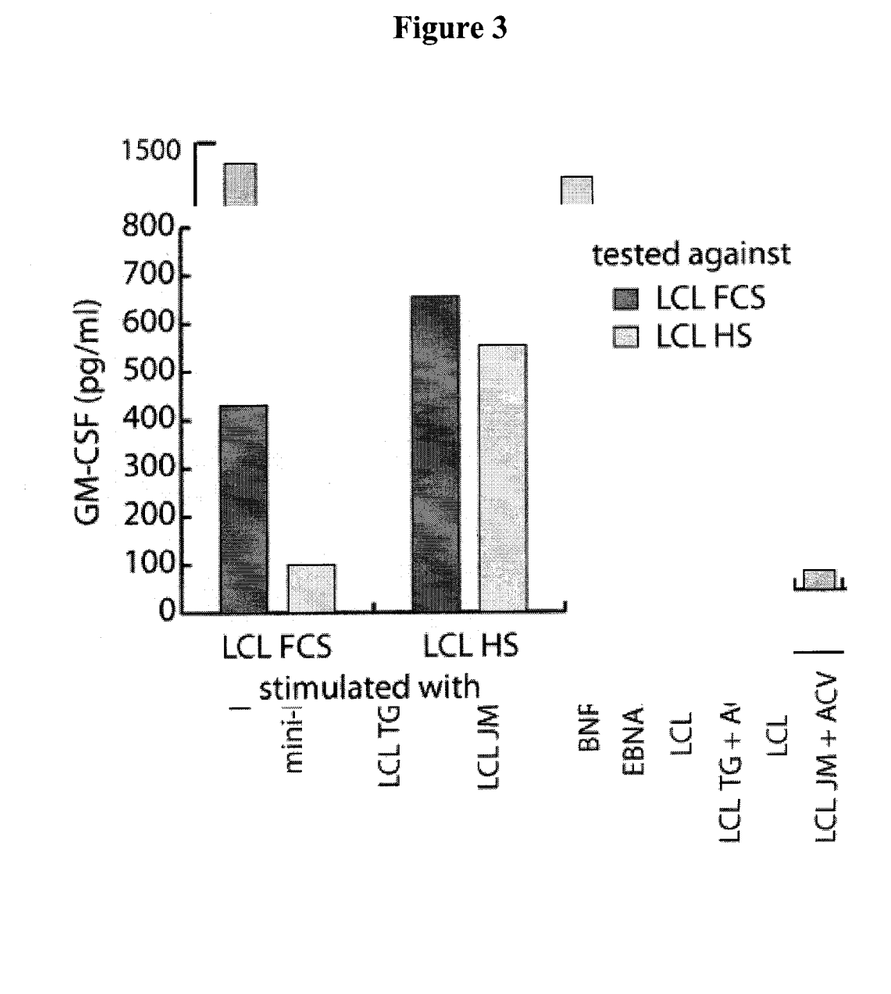

3. Preferential Expansion of FCS-Reactive CD4+ T Cells upon Stimulation with LCL Cultured in FCS-Supplemented Media Because antigens presented on MHC class II molecules are mostly derived from exogenous proteins taken up by endocytosis, serum supplements in culture media might add to the variable expansion of EBV-specific CD4+ T cells after LCL stimulation. CD4+ T cells reacting to FCS-derived antigens have been described in numerous studies (11, 25, 26, 30), but it remained unknown whether FCS-specific CD4+ T cells prevail in LCL-stimulated CD4+ T cell cultures from virus carrying individuals. To address this question, LCL continuously grown in medium supplemented with either 10% FCS (LCL-FCS) or 10% human serum (LCL-HS) were used to stimulate autologous T cells. When tested against LCL-FCS and LCL-HS, all of the CD4+ T cell lines established from ten EBV-seropositive donors and five patients with IM by LCL-FCS stimulation responded preferentially against LCL-FCS. By contrast, T cell lines stimulated with LCL-HS recognized both types of target cells, indicating that they target viral or cellular antigens rather than serum supplements (FIG. 3). These results suggested that FCS-specific T cells may dominate LCL-stimulated CD4+ T cell cultures and that in order to obtain T cell lines enriched in CD4+ T cells specific for EBV antigens, FCS has to be omitted from culture media.

4. Serum from EBV-Seropositive Donors Impairs Antigen Transfer by Virions.

Figure 4:
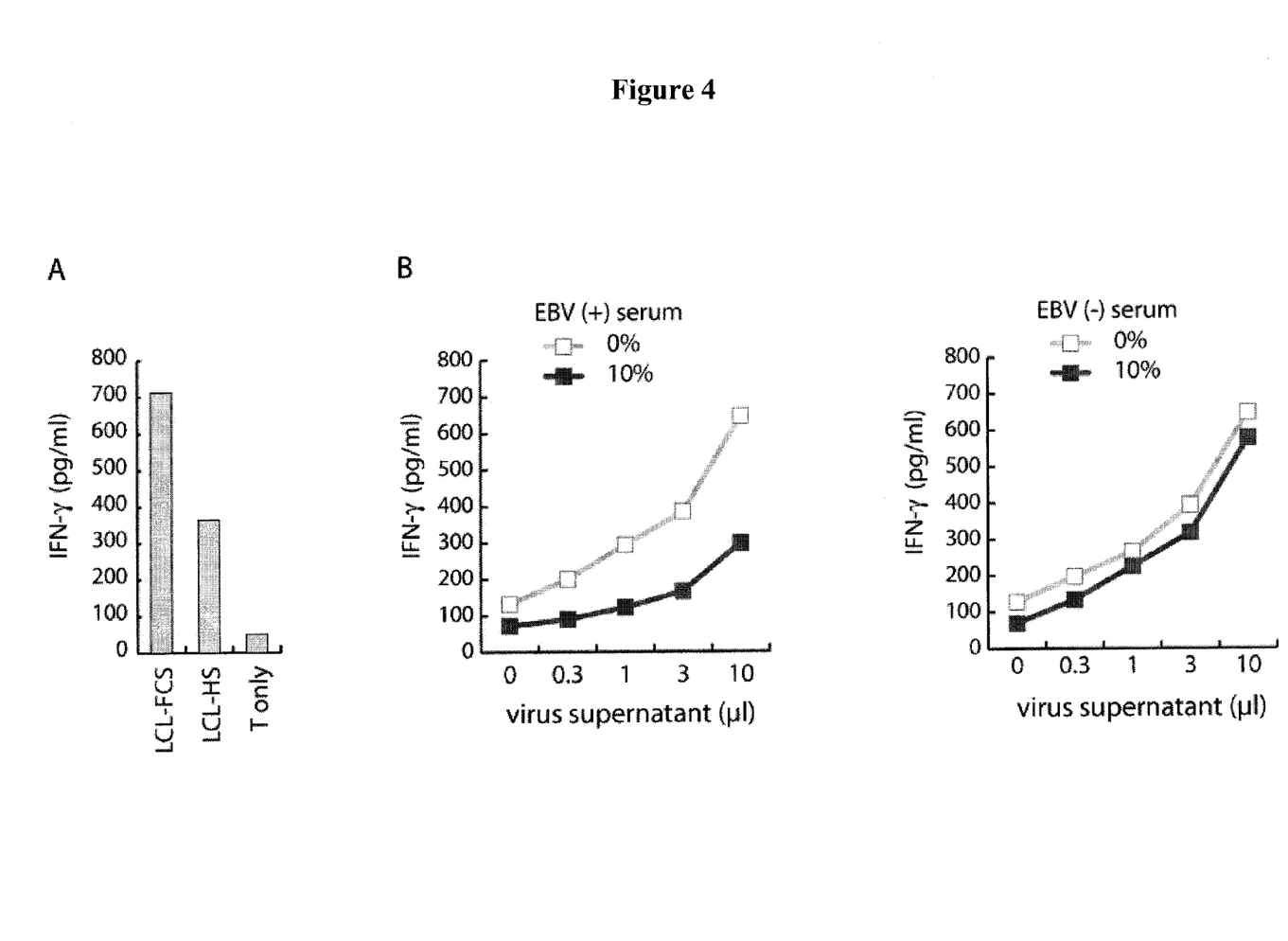

These results implied that the individual CD4+ T cell response to FCS probably impacts on the expansion of CD4+ component in LCL-stimulated T cell preparation and that the proportion of EBV-specific CD4+ T cells might be increased when human serum instead of FCS was used as media supplement. However, when LCL-HS and LCL-FCS were tested for recognition by T cell clones specific for structural antigens of EBV, LCL-HS were often recognized to a lesser extent (FIG. 4A). Antibodies against structural antigens are known to circulate in serum of EBV-infected subjects and might interfere with CD21-mediated virus-uptake and hence the presentation of virion antigens by LCL (38). To test this hypothesis, virus supernatant of the B95.8 cell line was either left untreated or incubated with human serum either derived from an EBV-seropositive (EBV+) or EBV-seronegative (EBV−) donor at a final concentration of 10% for 2 hours, and subsequently pulsed at increasing concentrations onto mini-LCL. After 24 hours of incubation, virus-pulsed mini-LCL were tested for recognition by virion-specific T cells. Compared to untreated controls, serum from EBV-positive donors reduced T cell recognition while serum from an EBV-negative donor had no effect (FIG. 4B). These results suggested that serum from EBV-positive donors contains components that specifically affect virion antigen presentation, most likely antibodies that block receptor-mediated uptake of viral particles. This inhibitory effect was overcome with higher amounts of EBV particles, probably because anti-viral antibodies become limiting (data not shown).

5. Efficient Presentation of Structural Antigens Derived from VLP.

Figure 5:
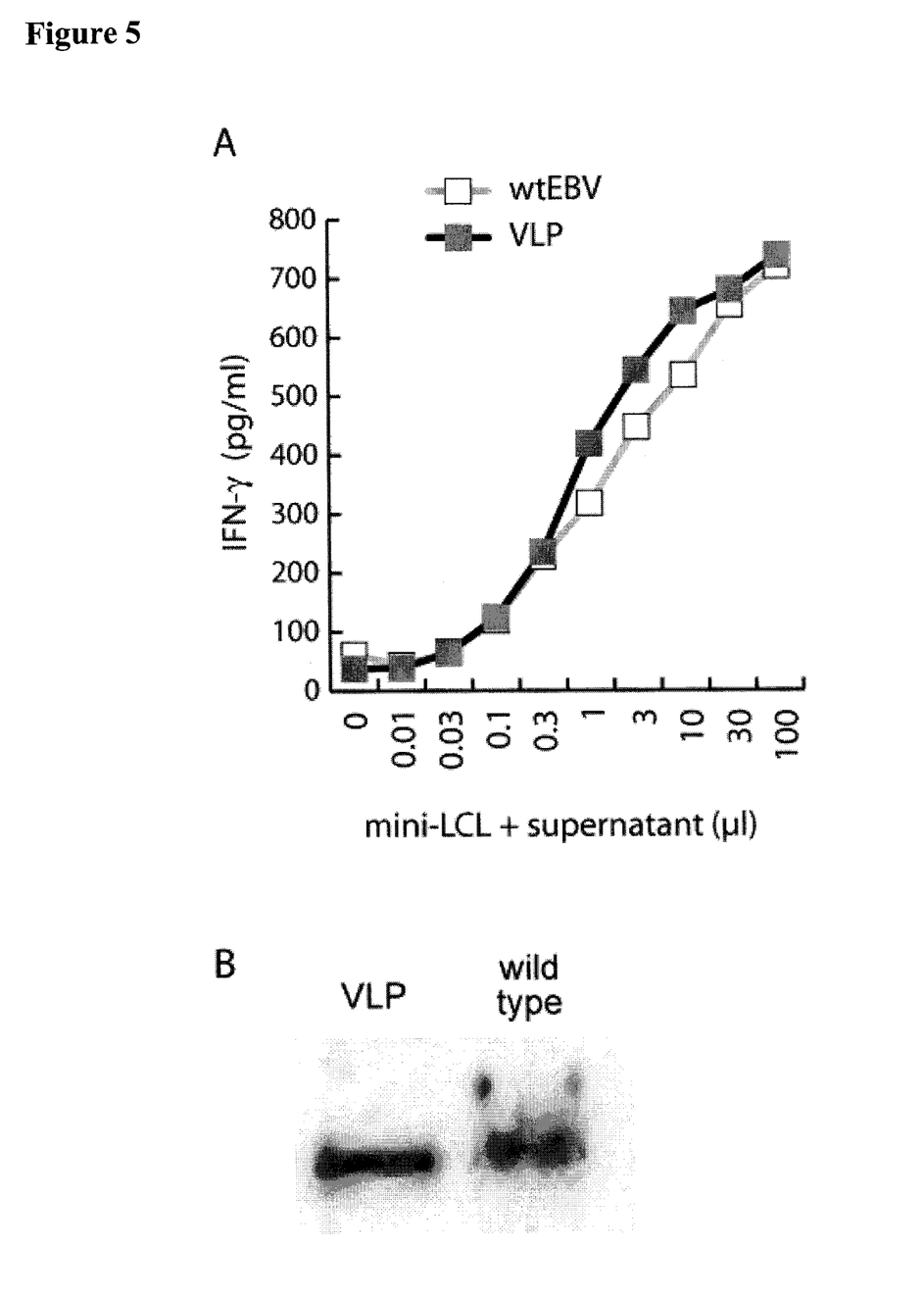

These results indicated that virus neutralizing activity in human serum may compromise the expansion of EBV-specific CD4+ T cells by LCL-HS stimulation, and that these limitations may be overcome by pulsing LCL with excess virus particles. Such a protocol would also compensate for the differences in virus production by LCL and conduce to standardized stimulation conditions. Because safety concerns preclude the addition of wild-type virus supernatant to stimulator LCL, we assessed whether EBV virions devoid of viral DNA i.e. virus-like particles (VLP) are able to transfer virion antigens. Large amounts of VLP are produced upon induction of the lytic cycle in the 293/TR− cell line, which carries an EBV genome that lacks the terminal repeats required for packaging viral DNA into virions (19). Thus, VLP are incapable of transforming primary human B cells in vitro (10). Mini-LCL were pulsed with increasing amounts of VLP or wtEBV and subsequently tested for recognition by BLLF1-specific CD4+ T cells (FIG. 5). VLP and wtEBV-pulsed mini-LCL were recognized with similar efficiency, demonstrating that VLP are able to transfer antigen. Similar results were obtained with a CD4+ T cell clone specific for the tegument protein BNRF1 (data not shown).

6. Virion-Specific CD4+ T Cells are Efficiently Expanded by Repeated Stimulation with VLP-Pulsed PBMC In Vitro.

Figure 6:
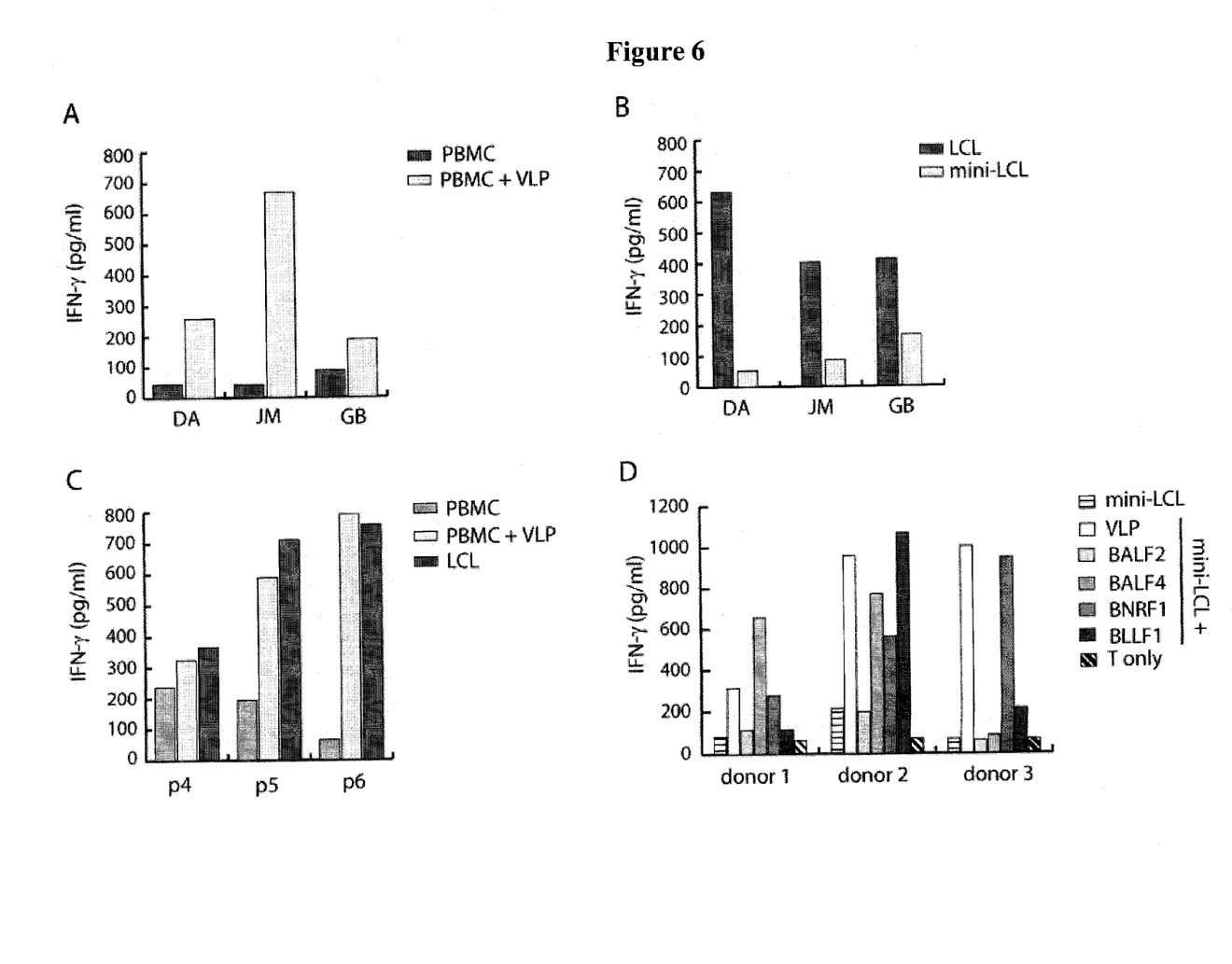

Primary B cells express CD21 and are capable of presenting virion antigens following receptor-mediated virus uptake (2), implying that VLP-pulsed PBMC could be used as APCs to expand virion-specific CD4+ T cells. Such protocols would obviate the lengthy procedure of establishing LCL and thereby shorten the T cell preparation procedure significantly. To address this possibility, CD4+ T cells from peripheral blood of three EBV(+) healthy donors were stimulated with autologous PBMCs that had been pulsed with VLP from TR− cells cultured in serum-free medium. After five to six rounds of stimulation the majority of cells within the VLP-stimulated T cell lines reacted against VLP-pulsed but not unpulsed PBMC, and against autologous LCL but not mini-LCL, indicating that they were specific for EBV structural antigens (FIG. 6A, B). This selective reactivity against VLP-pulsed PBMC and LCL was observed after four to six restimulations (FIG. 6C), which is much faster than with LCL-stimulation (1). Structural antigen specificity of these T cell lines was verified by pulsing mini-LCL with single recombinant lytic cycle proteins and testing the cells for recognition by the T cells (FIG. 6D). Each line recognized at least one of the structural antigens tested, demonstrating that VLP-pulsed PBMC are able to reactivate and expand virion antigen-specific CD4+ T cells.

7. Highly Efficient Ex Vivo Expansion of EBV-Specific CD4+ T Cells Using VLP-Pulsed PBMC.

Figure 7:
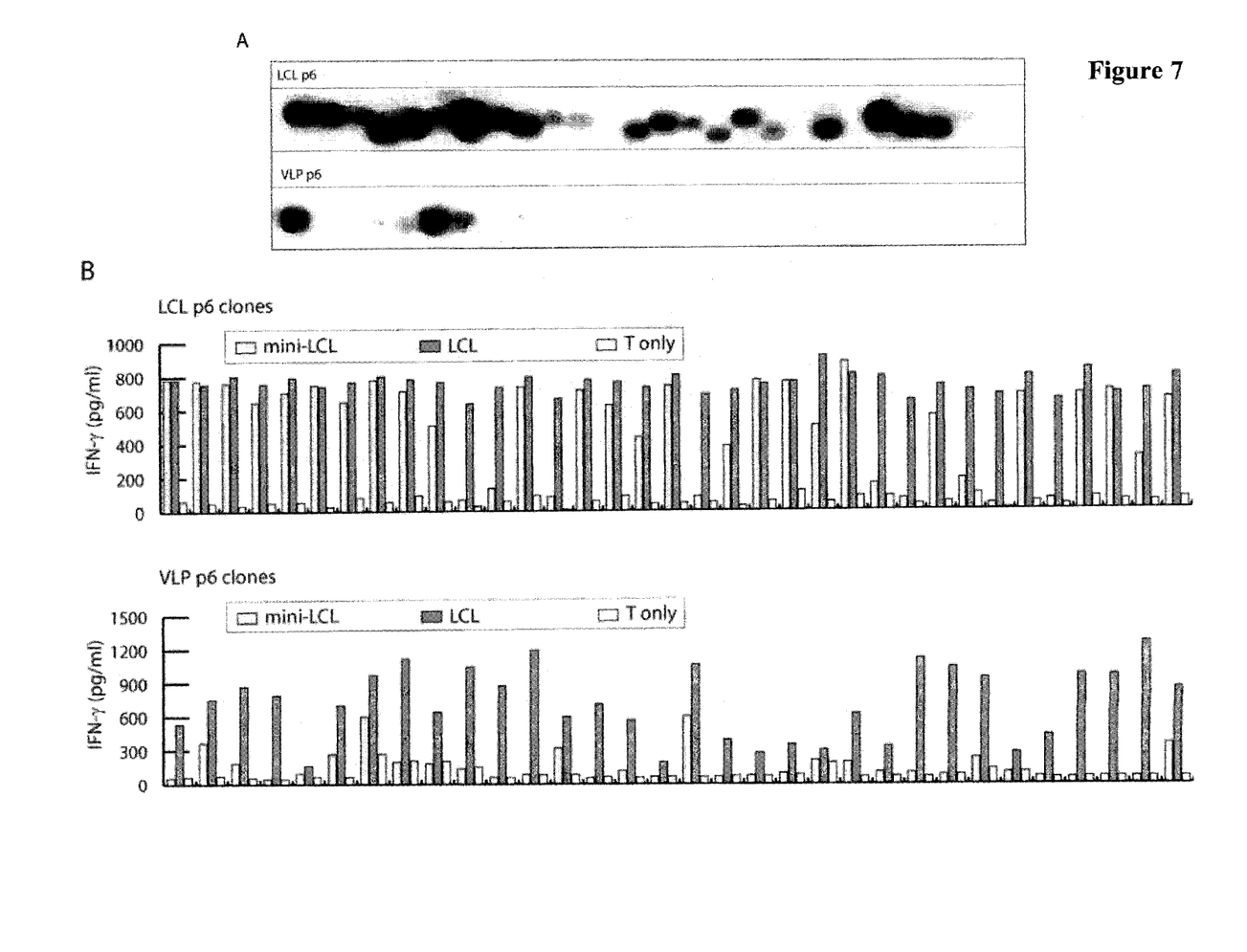

In a final set of experiments we sought to compare the efficiency of expansion of EBV-specific CD4+ T cells following stimulation with either VLP-pulsed PBMC or LCL that had been cultured in medium supplemented with human serum. After six rounds of stimulations, the breadth of the T cell response was assessed by analyzing T cell receptor V beta chain expression. As shown in FIG. 7A, CD4+ T cell lines from donor GB at passage six were oligoclonal when stimulated with VLP-pulsed PBMC but polyclonal when stimulated with LCL. To define the specificities of these T cells, the lines were cloned by limiting dilution and outgrowing cultures tested for recognition of autologous LCL versus autologous mini-LCL. Most of the clones that were derived from the T cell lines stimulated with VLP-pulsed PBMC recognized EBV lytic cycle antigens as indicated by the selective recognition of LCL (FIG. 7B). In contrast, the majority of clones derived from LCL-stimulated T cell lines reacted against LCL and mini-LCL and therefore recognized non-lytic cycle antigens. Since the majority of endogenous latent EBV antigens are not efficiently presented on MHC class II (1, 23), these CD4+ T cells most likely recognized cellular antigens. Similar results were obtained with T cell lines from the two additional EBV(+) donors (data not shown). In conclusion, EBV-specific CD4+ T cells were much more efficiently expanded when VLP-pulsed PBMC rather than LCL were used as stimulator cells.

SUMMARY

The recent identification of low endogenous CD4+ T cell numbers as an important risk factors for the development of EBV-associated diseases in immunosuppressed patients (36), and of better clinical responses in patients with PTLD receiving EBV-specific T cell lines that contained higher proportions of CD4+ T cells (15), imply an important role for CD4+ T cell in the control of EBV infection in vivo. EBV-specific CD4+ T cells in LCL-stimulated T cell preparations are almost exclusively directed against structural antigens of the virus (1), which are efficiently presented on MHC II following receptor-mediated uptake of released viral particles (2). These T cells are cytolytic and able to inhibit the outgrowth of LCL from newly EBV-infected B cells in vitro (16). Because the CD4/CD8 ratio in LCL-stimulated T cell preparations is highly variable (37), this study aimed to define factors that impact on the in vitro expansion of EBV-structure antigen-specific CD4+ T cells and to deduce strategies for the efficient ex vivo expansion of EBV-specific CD4+ T cells for future use in the treatment of EBV-associated diseases.

As measured by lytic cycle protein expression, between 0-5% of cells in LCL cultures spontaneously become permissive for lytic viral replication (19). Within the group of LCLs analysed, the number of DNA-containing viral particles in cell culture supernatants varied about 40-fold, and these differences were reflected by a variable CD4+ T cell recognition ranging from strong to undetectable. Thus, intrinsically low virus production by LCL may compromise the expansion of lytic cycle antigen-specific CD4+ T cells and contribute to the variable CD4+ ratio in LCL-stimulated T cell preparations.

The use of FCS as media supplement for culturing LCL for immunological applications has always been a major concern since FCS-reactive CD4+ T cells have been isolated from peripheral blood of many donors, but it remained unknown whether FCS-reactive T cells would constitute a significant proportion of the LCL-expanded CD4+ T cell population (25, 26). All CD4+ T cell lines that were repeatedly stimulated with LCL grown in FCS-supplemented media eventually showed FCS-reactivity, even lines established from patients with acute IM who are expected to have a strong antiviral T cell response. Although it is currently not known whether interindividual differences in FCS-specific CD4+ T cell precursor frequencies exist and contribute to the variable CD4/CD8 ratio in LCL-stimulated T cell preparations, such T cells probably compromise clinical efficacy of EBV-specific T cell preparations by diminishing the number of virus-specific effectors. Xenogenic immune responses are precluded when stimulator LCL are cultured in serum-free media or media supplemented with human serum, but despite new and improved media formulations, efficient propagation of LCL still requires addition of serum (11). Owing to the high rate of EBV infestation in the adult population, human serum is usually derived from EBV-positive donors. Since EBV infection elicits strong Immoral immune responses against many viral proteins, including glycoproteins essential for viral host cell adsorption and penetration (32), human serum may impair uptake and subsequent presentation of virion antigens on MHC II. In fact, serum from EBV(+) but not EBV(−) donors diminished T cell recognition when B cells were pulsed with low viral titers, suggesting that human serum impairs the presentation of virion antigens when viral particles become limiting, e.g. when virus production by stimulator LCL is intrinsically low, or when LCL are treated with acyclovir to reduce virus production as currently performed in most clinical protocols (4, 33).

These findings indicated that addition of excess amounts of EBV particles may antagonize the inhibitory effect of human serum and compensate for differences in virus production by different LCLs, and thereby facilitate to establish uniform and standardized stimulation conditions. Because incubation of stimulator cells with wtEBV would pose an incalculable health risk to patients, the possibility of using genome-deficient EBV VLP was explored. EBV VLP produced by human cells in serum-free media are readily available in large quantities and transfer structural antigens as efficiently as wtEBV. Instead of LCL, PBMC pulsed with VLP were used as stimulators because PBMC do not produce virus and are immediately available. Most importantly, stimulation of CD4+ T cells with LCL causes expansion of virus-specific as well as autoreactive CD4+ T cells (1, 13). Consequently, LCL-stimulated CD4+ T cell lines usually require 10-20 rounds of stimulation to become EBV-specific (1). Because PBMC pulsed with VLP efficiently expanded virus-specific but not autoreactive CD4+ T cells, EBV-specific CD4+ T cell lines were already obtained after four to six restimulations.

VLP-based vaccines have been successfully used to elicit immune responses against different viruses in vivo, most notably HPV (5, 39). Our results demonstrate that VLP are also useful to expand antigen-specific T cells in vitro, especially in those cases where the number of known viral CD4+ T cell epitopes is too small to allow for peptide-based approaches.

REFERENCES

1. Adhikary, D., U. Behrends, H. Boerschmann, A. Pfunder, S. Burdach, A. Moosmann, K. Witter, G. W. Bornkamm, and J. Mautner. 2007. Immunodominance of Lytic Cycle Antigens in Epstein-Barr Virus-Specific CD4+ T Cell Preparations for Therapy. PLoS ONE 2:e583.
2. Adhikary, D., U. Behrends, A. Moosmann, K. Witter, G. W. Bornkamm, and J. Mautner. 2006. Control of Epstein-Barr virus infection in vitro by T helper cells specific for virion glycoproteins. J Exp Med 203:995-1006.
3. Bevan, M. J. 2006. Cross-priming. Nat Immunol 7:363-5.
4. Bollard, C. M., I. Kuehnle, A. Leen, C. M. Rooney, and H. E. Heslop. 2004. Adoptive immunotherapy for posttransplantation viral infections. Biol Blood Marrow Transplant 10:143-55.
5. Chackerian, B. 2007. Virus-like particles: flexible platforms for vaccine development. Expert Rev Vaccines 6:381-90.
6. Datta, A. K., B. M. Colby, J. E. Shaw, and J. S. Pagano. 1980. Acyclovir inhibition of Epstein-Ban virus replication. Proc Natl Acad Sci USA 77:5163-6.
7. Delecluse, H. J., T. Hilsendegen, D. Pich, R. Zeidler, and W. Hammerschmidt. 1998. Propagation and recovery of intact, infectious Epstein-Barr virus from prokaryotic to human cells. Proc Nati Acad Sci USA 95:8245-50.
8. Delecluse, H. J., D. Pich, T. Hilsendegen, C. Baum, and W. Hammerschmidt. 1999. A first-generation packaging cell line for Epstein-Barr virus-derived vectors. Proc Natl Acad Sci USA 96:5188-93.
9. Feederle, R., B. Neuhierl, G. Baldwin, H. Bannert, B. Hub, J. Mautner, U. Behrends, and H. J. Delecluse. 2006. Epstein-Barr virus BNRF1 protein allows efficient transfer from the endosomal compartment to the nucleus of primary B lymphocytes. J Virol 80:9435-43.
10. Feederle, R., C. Shannon-Lowe, G. Baldwin, and H. J. Delecluse. 2005. Defective infectious particles and rare packaged genomes produced by cells carrying terminal-repeat-negative epstein-barr virus. J Virol 79:7641-7.
11. Gallot, G., S. Valiant, R. Vivien, B. Clemenceau, C. Ferrand, P. Tiberghien, J. Gaschet, N. Robillard, and H. Vie. 2006. Selection of Epstein-Barr virus specific cytotoxic T lymphocytes can be performed with B lymphoblastoid cell lines created in serum-free media. Clin Exp Immunol 144:158-68.
12. Gottschalk, S., C. M. Rooney, and H. E. Heslop. 2005. Post-transplant lymphoproliferative disorders. Annu Rev Med 56:29-44.
13. Gudgeon, N. H., G. S. Taylor, H. M. Long, T. A. Haigh, and A. B. Rickinson. 2005. Regression of Epstein-Barr virus-induced B-cell transformation in vitro involves virus-specific CD8+ T cells as the principal effectors and a novel CD4+ T-cell reactivity. J Virol 79:5477-88.
14. Gussoni, E., M. A. Panzara, and L. Steinman. 1997. Evaluating Human T Cell Receptor Gene Expression by PCR, Current Protocols in Immunology. John Wiley & Sons, Inc.
15. Hague, T., G. M. Wilkie, M. M. Jones, C. D. Higgins, G. Urquhart, P. Wingate, D. Burns, K. McAulay, M. Turner, C. Bellamy, P. L. Amlot, D. Kelly, A. Macgilchrist, M. K. Gandhi, A. J. Swerdlow, and D. H. Crawford. 2007. Allogeneic cytotoxic T cell therapy for EBV-positive post transplant lymphoproliferative disease: results of a phase II multicentre clinical trial. Blood. 110:1123-31.
16. Heller, K. N., C. Gurer, and C. Munz. 2006. Virus-specific CD4+ T cells: ready for direct attack. J Exp Med 203:805-8.
17. Hislop, A. D., G. S. Taylor, D. Sauce, and A. B. Rickinson. 2007. Cellular responses to viral infection in humans: lessons from Epstein-Barr virus. Annu Rev Immunol 25:587-617.
18. Junying, J., K. Herrmann, G. Davies, D. Lissauer, A. Bell, J. Timms, G. M. Reynolds, S. G. Hubscher, L. S. Young, G. Niedobitek, and P. G. Murray. 2003. Absence of Epstein-Barr virus DNA in the tumor cells of European hepatocellular carcinoma. Virology 306:236-43.
19. Kieff, E., A. B. Rickinson. 2006. Epstein-Barr virus and its replication. In *Field's Virology*. 5$^{th}$ ed. D. M. Knipe, and P. M. Howley, eds. Lippincott-Raven, Philadelphia, Pa. 2603-2654.
20. Kuppers, R. 2003. B cells under influence: transformation of B cells by Epstein-Barr virus. Nat Rev Immunol 3:801-12.
21. Laichalk, L. L., and D. A. Thorley-Lawson. 2005. Terminal differentiation into plasma cells initiates the replicative cycle of Epstein-Barr virus in vivo. J Virol 79:1296-307.
22. Landais, E., X. Saulquin, and E. Houssaint. 2005. The human T cell immune response to Epstein-Barr virus. Int J Dev Biol 49:285-92.
23. Mautner, J., D. Pich, F. Nimmerjahn, S. Milosevic, D. Adhikary, H. Christoph, K. Witter, G. W. Bornkamm, W. Hammerschmidt, and U. Behrends. 2004. Epstein-Barr virus nuclear antigen 1 evades direct immune recognition by CD4+ T helper cells. Eur J Immunol 34:2500-9.
24. Milosevic, S., U. Behrends, D. Adhikary, and J. Mautner. 2006. Identification of major histocompatibility complex class II-restricted antigens and epitopes of the Epstein-Barr virus by a novel bacterial expression cloning approach. J Virol 80:10357-64.
25. Misko, I. S., R. G. Kane, and J. H. Pope. 1981. Generation in vitro of EBV-induced specific cytotoxic T cells in autologous serum avoids complications due to self-preferred foetal calf serum-specific T-cell cytotoxicity. Int J Cancer 27:513-9.
26. Misko, I. S., J. H. Pope, R. G. Kane, H. Bashir, and T. Doran. 1982. Evidence for the involvement of HLA-DR antigens in restricted cytotoxicity by fetal calf serum-specific human T cells. Hum Immunol 5:183-97.
27. Moosmann, A., N. Khan, M. Cobbold, C. Zentz, H. J. Delecluse, G. Hollweck, A. D. Hislop, N. W. Blake, D. Croom-Carter, B. Wollenberg, P. A. Moss, R. Zeidler, A. B. Rickinson, and W. Hammerschmidt. 2002. B cells immortalized by a mini-Epstein-Barr virus encoding a foreign antigen efficiently reactivate specific cytotoxic T cells. Blood 100:1755-64.
28. Moss, P., and A. Rickinson. 2005. Cellular immunotherapy for viral infection after HSC transplantation. Nat Rev Immunol 5:9-20.
29. Nimmerjahn, F., S. Milosevic, U. Behrends, E. M. Jaffee, D. M. Pardoll, G. W. Bornkamm, and J. Mautner. 2003. Major histocompatibility complex class II-restricted presentation of a cytosolic antigen by autophagy. Eur J Immunol 33:1250-9.
30. Ostler, T., and S. Ehl. 2002. A cautionary note on experimental artefacts induced by fetal calf serum in a viral model of pulmonary eosinophilia. J Immunol Methods 268:211-8.
31. Pudney, V. A., A. M. Leese, A. B. Rickinson, and A. D. Hislop. 2005. CD8+ immunodominance among Epstein-Barr virus lytic cycle antigens directly reflects the efficiency of antigen presentation in lytically infected cells. J Exp Med 201:349-60.
32. Rickinson, A. B., and E. Kieff. 2006. Epstein-Barr virus. In *Field's Virology*, 5$^{th}$ ed. D. M. Knipe and P. M. Howley, eds. Lippincott-Raven, Philadelphia, Pa. 2655-2700.
33. Rooney, C. M., M. A. Roskrow, C. A. Smith, M. K. Brenner, and H. E. Heslop. 1998. Immunotherapy for Epstein-Barr virus-associated cancers. J Natl Cancer Inst Monogr: 89-93.
34. Rooney, C. M., C. A. Smith, C. Y. Ng, S. Loftin, C. Li, R. A. Krance, M. K. Brenner, and H. E. Heslop. 1995. Use of gene-modified virus-specific T lymphocytes to control Epstein-Barr-virus-related lymphoproliferation. Lancet 345:9-13.
35. Rooney, C. M., C. A. Smith, C. Y. Ng, S. K. Loftin, J. W. Sixbey, Y. Gan, D. K. Srivastava, L. C. Bowman, R. A. Krance, M. K. Brenner, and H. E. Heslop. 1998. Infusion of cytotoxic T cells for the prevention and treatment of Epstein-Barr virus-induced lymphoma in allogeneic transplant recipients. Blood 92:1549-55.
36. Sebelin-Wulf, K., T. D. Nguyen, S. Oertel, M. Papp-Vary, R. U. Trappe, A. Schulzki, A. Pezzutto, H. Riess, and M. Subklewe. 2007. Quantitative analysis of EBV-specific CD4/CD8 T cell numbers, absolute CD4/CD8 T cell numbers and EBV load in solid organ transplant recipients with PLTD. Transpl Immunol 17:203-10.
37. Smith, C. A., C. Y. Ng, H. E. Heslop, M. S. Holladay, S. Richardson, E. V. Turner, S. K. Loftin, C. Li, M. K. Brenner, and C. M. Rooney. 1995. Production of genetically modified Epstein-Barr virus-specific cytotoxic T cells for adoptive transfer to patients at high risk of EBV-associated lymphoproliferative disease. J Hematother 4:73-9.
38. Thorley-Lawson, D. A., and C. A. Poodry. 1982. Identification and isolation of the main component (gp350-gp220) of Epstein-Barr virus responsible for generating neutralizing antibodies in vivo. J Virol 43:730-6.
39. Xu, Y. F., Y. Q. Zhang, X. M. Xu, and G. X. Song. 2006. Papillomavirus virus-like particles as vehicles for the delivery of epitopes or genes. Arch Virol 151:2133-48.

The invention claimed is:
1. An ex vivo method for producing a preparation containing CD4+ T cells specific for EBV structural antigens, the method comprising
incubating B cells with preparations of Epstein-Barr virus-like particles (EB-VLPs) containing EBV structural antigens and devoid of transforming EBV DNA for a time period sufficient to generate a preparation containing B cells presenting EBV structural antigens, wherein said B cells are primary B cells;
admixing said B cells presenting EBV structural antigens with a preparation containing T cells including CD4+ T cells;
incubating said admixture to obtain a preparation including CD4+ T cells specific for EBV structural antigens; optionally
isolating and expanding said CD4+ T cells specific for EBV structural antigens to obtain a population of CD4+ T cells specific for EBV structural antigens.
2. The method according to claim 1, wherein said B cells are primary B cells contained in or isolated from a peripheral blood mononucleated cells (PBMCs) containing preparation.
3. The method according to claim 1 or claim 2, wherein said preparation containing T cells including CD4+ T cells is contacted with said preparation containing B cells presenting EBV structural antigens at least two times, preferably 4 to 8 times.
4. The method according to claim 3, wherein said primary B cells are obtained from peripheral blood or bone marrow.
5. The method according to claim 3, wherein said primary B cells are obtained from an autologous donor.
6. The method according to claim 3, wherein said T cells containing preparation including CD4+ T cells is obtained from an autologous donor from whom the B cells are obtained.
7. The method according to claim 2, wherein said peripheral blood mononucleated cells are additionally treated with immunodominant CD8+ T cell epitopes of the immediate early and early lytic cycle proteins or EBNA3 proteins to generate EBV specific CD8+ T cells together with CD4+ T cells.
8. The method according to claim 1, wherein the Epstein-Barr virus-like particles (EB-VLPs) are devoid of EBV DNA.

* * * * *